United States Patent [19]

Peters

[11] 4,383,534

[45] May 17, 1983

[54] VITAL SIGNS MONITORING APPARATUS

[76] Inventor: Jeffrey L. Peters, 2735 Sherwood Dr., Salt Lake City, Utah 84108

[21] Appl. No.: 156,648

[22] Filed: Jun. 5, 1980

[51] Int. Cl.$^3$ .............................................. A61B 5/00
[52] U.S. Cl. .................................. 128/671; 128/715; 128/207.15
[58] Field of Search ............................... 128/670–671, 128/715, 773, 782, 207.14–207.15, 349 R, 349 BV, 419, 419 D

[56] References Cited

U.S. PATENT DOCUMENTS

| | | | |
|---|---|---|---|
| 3,499,434 | 3/1970 | Ullrich et al. | 128/670 |
| 3,734,094 | 5/1973 | Calinog | 128/207.15 X |
| 4,046,139 | 9/1977 | Horn | 128/736 |
| 4,088,138 | 5/1978 | Diack et al. | 128/671 |
| 4,176,660 | 12/1979 | Mylrea et al. | 128/671 |
| 4,185,638 | 1/1980 | Bruner | 128/207.15 X |
| 4,248,241 | 2/1981 | Tacchi | 128/671 |

OTHER PUBLICATIONS

*Medtronics Brochure*: "Telecor Esophageal Temperature & ECG Monitor" Medtronics Inc., 3055 Highway 8, Minneapolis, Minn.
"A Patient Monitor" New Inventions Section, The Lancet, Oct. 13, 1962, p. 759.
Geddes, L. A. et al., "Acquisition of Physiologic Data at the Bedside," Amer. Jrnl. Med. Electronics, Jan.–May 1962, pp. 62–69.
Osborne, J. J. et al., "Measurement and Monitoring of Acutely Ill Patients by Digital Computer," *Surgery*, Dec. 1968, p. 1057.

*Primary Examiner*—Kyle L. Howell
*Assistant Examiner*—Francis J. Jaworski
*Attorney, Agent, or Firm*—Trask & Britt

[57] ABSTRACT

An endotracheal tube has detection devices including a temperature detector, ECG detector and the heart sounds and breath sounds detector positioned proximate the interior end of the tube. A chassis is postioned exterior the patient within audio and visual range of the user. The detectors are connected through the exterior end of the endotracheal tube to the chassis to transmit signals that are vital. The chassis has means to display and broadcast the visual and audio signals. A blood pressure sensing device is also connected to the chassis to display the blood pressure of a patient. The endotracheal tube has a cuff positioned proximate its interior end. A connector is connected into the inflation means to detect cuff pressure and to the chassis to display cuff pressure. The remote respiratory system is connected to the endotracheal tube and has detectors associated therewith to detect selected parameters of the respiratory system. The detectors are selectively connected to the chassis to display the detected parameters. The chassis has an internal power supply and is portable with the patient.

20 Claims, 5 Drawing Figures

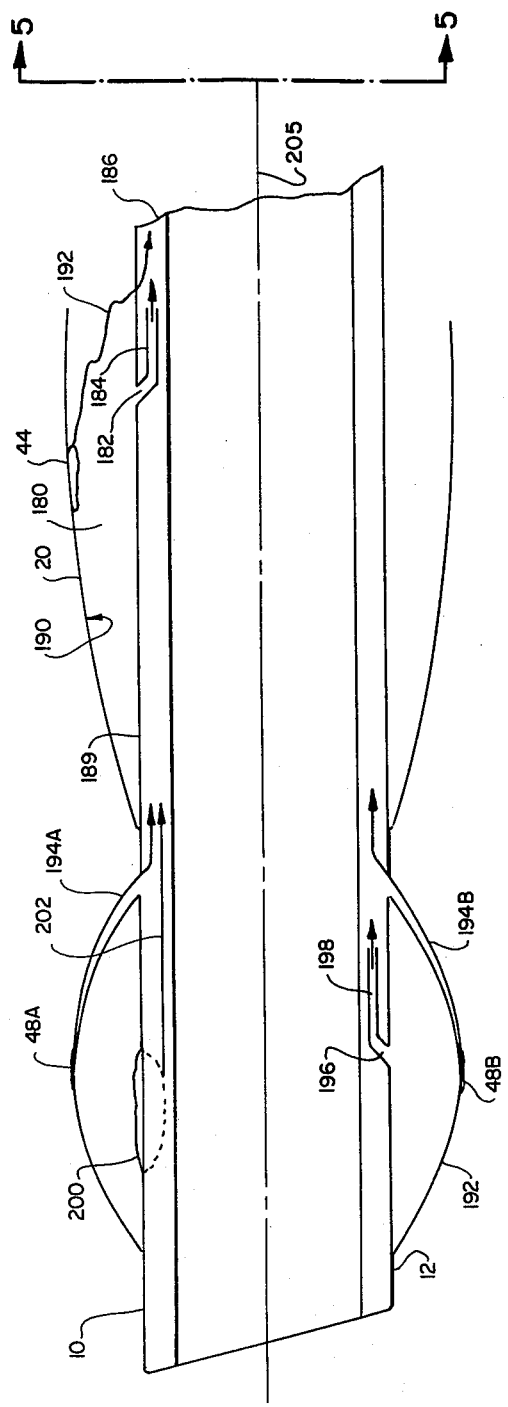

VITAL SIGNS MONITORING APPARATUS

BACKGROUND OF THE INVENTION

1. Field

This invention relates to medical devices for measuring indicia, and more particularly to devices and apparatus for measuring a plurality of vital signs and centrally displaying the vital signs to a user.

2. State of the Art

In an operating room environment, an anesthesiologist may be charged with the responsibility of monitoring various vital signs of the patient upon whom an operation is being performed. These vital signs may include body temperature, heart rate, respiration or breath rate, blood pressure and other related vital life signs of a patient. Presently, the vital life signs are monitored by a variety of different devices with detection effected from a variety of differently placed sensors. An external ECG (electrocardiogram) connection may be made to a remotely located ECG device. Heart sounds and breath sounds may be monitored with a stethoscope or perhaps ignored depending upon the circumstances and the nature of the operation being performed. The blood pressure may be monitored by conventional blood pressure apparatus together with a stethoscope to determine or detect Korotkoff sounds. The body temperature may be monitored by a rectal or nasal pharyngeal thermometer or other thermometer as determined by the nature of the operation to be performed. In addition to monitoring of vital signs, the anesthesiologist will frequently be required to monitor the respiratory system which is being used to control the patient's respiration and the supply of oxygen to the patient.

Presently, the vital signs to be monitored by the anesthesiologist are monitored by diverse apparatus positioned in and about the operating room environment. Distractions, interruptions or exigencies of the operation being performed may preclude or prevent the anesthesiologist from effectively or properly monitoring the various displays. Yet, it is typically recognized that monitoring of these displays is essential. A distinct morbidity rate may be related to a failure to monitor these vital life signs on a continuing basis. The vital signs are the first indication of a problem and/or the need to modify operative procedures in order to preserve the patient's life. Subsequent to an operation, a patient is moved from the operating room to a recovery room, an intensive care room or some other similar facility. During the move, the patient may not be monitored. Some patient deaths could conceivably be avoided if one were able to monitor some of the vital life signs.

No present devices have been constructed which will permit continuous monitoring of a variety of different vital signs essential to the initial diagnosis of a patient problem hazardous to the patient's life, both during the operating itself as well as subsequently while the patient is in transport to and further while the patient is in a recovery room or intensive care environment. A variety of different devices have been used. However, a centralized simple portable device has heretofore not been constructed. Such a device is highly desirable. Further, a device having a centralized detection location covering a multitude of operations is particularly desirable. Such will facilitate the monitoring of vital life signs and minimize the morbidity associated with operative procedures performed on a patient.

SUMMARY OF THE INVENTION

A life signs monitoring apparatus includes means for positioning a detector in the trachea of a patient. The positioning means is preferably an endotracheal tube with sound detection means adapted thereto proximate the interior or proximal end to detect heartbeat and breath sounds and to transmit signals reflective thereof. Transmission means is connected to the detection means and extends along the length of the tube and away from the exterior or distal end of the tube. The transmission means receives and transmits the heartbeat and breath signals for audible monitoring by the user.

A chassis is preferably positioned within audible and visual range of the user. Transmitting means to receive the heartbeat and breath sounds and process them for audible monitoring by the user is positioned within the chassis. The transmitting means includes second transmission means removably connected to the first transmission means and to the chassis to communicate the heart and breath sounds therebetween. Broadcast means are positioned within the chassis to receive the heart and breath sounds and broadcast them for audible monitoring by the user and other personnel attending the patient.

A vital signals monitoring system further includes blood pressure measuring means. The blood pressure measuring means includes a blood pressure detecting device for positioning at a blood pressure detection site. A pressure bulb is connected to the chassis for operation by the user. A blood pressure indicator is mounted to the chassis to indicate the blood pressure upon detection thereof. The indicator and bulb are connected by interconnecting tubing.

The vital signs detection system further includes electrocardiogram (ECG) sensing means adapted to the tube proximate the interior end. ECG display means are positioned within the chassis to receive and process and visually display the ECG signals. Conductor means interconnect the sensing means to the ECG display means. A power supply is positioned within the chassis to power the ECG display means.

The vital signs monitoring system also preferably includes temperature sensing means adapted to the tube proximate the interior end thereof. Temperature display means is positioned within the chassis to receive, process and visually display temperature reflective signals. Interconnecting conductors connect the sensing means to the chassis to transmit temperature reflective signals thereto.

The endotracheal tube may have a cuff positioned proximate the interior or proximal end with inflating means exterior the patient and in communication with the cuff for operation by the user to inflate and deflate the cuff. A connector is adapted to sense tube pressure. Tube cuff pressure indicator means is positioned within the chassis to visually indicate tube cuff pressure to the user. Interconnecting tube means connect the connector and the tube cuff pressure indicating means to transmit tube pressure to the indicating means.

In the preferred embodiment, the blood pressure sensing means also has a Korotkoff sound detection means positioned proximate the blood pressure detection means to connect the Korotkoff cuff sound detection means to the chassis to transmit Korotkoff sounds thereto. Means are positioned within the chassis to receive the Korotkoff cuff sounds and audibly broadcast them to the user.

In a highly preferred embodiment, the chassis includes a battery positioned within the chassis to act as the power supply. The chassis may include switch means to select Korotkoff sounds and the heart and breath sounds for broadcast to the user. The chassis may also have means to display heart rate signals and respiration rate signals for visual display to the user. The chassis may also have a graphic recorder and means to receive selected signals and display same graphically on the recorder. The chassis may also have means to receive signals from detector means positioned with respect to an external respiratory system and means to display selected parameters thereof for visual observation by the user.

BRIEF DESCRIPTION OF THE DRAWINGS

In the drawings, which illustrate the best mode presently contemplated for carrying out the invention.

FIG. 3 is an axial cross-sectional view of a part of an endotracheal tube for use with a vital signs monitoring apparatus of the instant invention;

FIG. 4 is a cross-sectional view of an endotracheal tube with use with a vital signs monitoring apparatus of the instant invention; and FIG. 5 is a cross-sectional view of another endotracheal tube for use with a vital signs monitoring apparatus of the instant invention.

DESCRIPTION OF THE ILLUSTRATED EMBODIMENT

Figure 1:
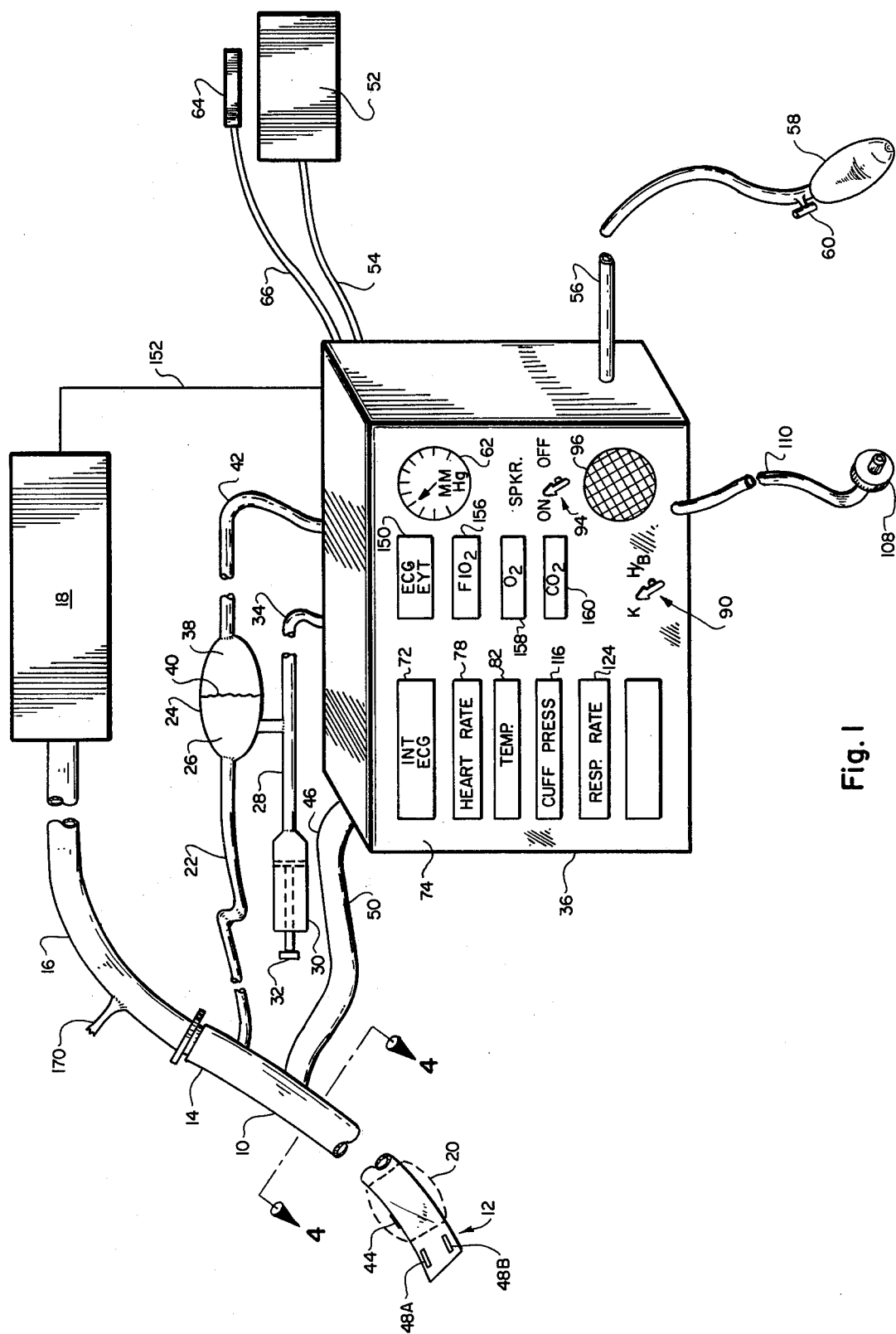
FIG. 1 is a simplified partially perspective representative illustration of the vital signs monitoring apparatus of the instant invention.

FIG. 1 illustrates an endotracheal tube 10 having an interior or proximal end generally illustrated by the number 12 and an exterior or distal end indicated by the number 14. In use, the endotracheal tube 10 is positioned through the mouth with the interior or proximal end inserted into the trachea of the patient. The exterior or distal end 14 is connected as here shown by a tube 16 to a respiratory control system 18. In practice, a preselected air or gas mixture is administered to the patient through the tube 16 and the tracheal tube 10 in a manner well known in the art.

The endotracheal tube 10 here shown has a cuff 20 positioned proximate its interior end 12 as shown. The cuff 20 is an inflatable and deflatable cuff which is inflated to effect a seal against the interior surfaces of the trachea so that the patient's respiration can be controlled through the respiratory system apparatus 18. The cuff 20 is connected through an interior channel to a tube 22 which extends away from the exterior end 14. As here illustrated, the tube 22 is connected, preferably removably connected, to a connector 24. The connector 24 has a first chamber 26 in direct communication with the tube 22. A second tube 28 is in direct communication with the first chamber 26. The second tube 28 is connected to means to operate the cuff which is here shown to be the aspirator 30. The aspirator 30 has a plunger 32 which upon operation thereof is used to inflate and deflate the tube cuff 20. A second tube 34 is connected to the tube 28. The other end of the tube 34 is connected to a chassis 36 for indication of tube cuff pressure, as more fully discussed hereinafter.

The connector 24 has a second chamber 38. The first chamber 26 is separated from the second chamber 38 by a flexible membrane 40 which is preferably any one of a variety of different flexible rubber membranes having low porosity characteristics. The membrane 40 is mounted to facilitate the transfer of sound therethrough. The second chamber 38 is connected by a tube 42 to the chassis 36. When the inflatable cuff 20 is in fact inflated, the cuff surface acts as a membrane of sorts to receive sounds interior of the body. In particular, breathing sounds or breath sounds are notably transmitted. Further, heart sounds including valve and ejection heart functioning is readily detectable and transmitted through the various substances of the body and transmitted through the tube 22 into the first chamber 26, through the membrane 40 and into the second chamber 38. The sounds are thereafter transmitted from the second chamber 38 through the tube 42, through the chassis 36 for processing and broadcast as more fully discussed hereinafter.

A temperature detector 44 may be positioned on the tube 10 proximate the interior end thereof to detect body temperature or core temperature. The temperature detector 44 may be positioned in a variety of locations, as more fully discussed hereinafter. The temperature detector 44 is connected via conductor 46 to the chassis 36 to transmit temperature reflective signals to the chassis for display thereof.

An electrocardiogram (ECG) sensing means may also be positioned proximate the interior end 12 of the endotracheal tube 10. The electrocardiogram sensing means, as here shown, are a pair of mylar strips 48A and 48B conductively connected through conductors 50 to the chassis 36 for processing and display of electrocardiogram (ECG) information.

FIG. 1 also shows blood pressure measuring means which has blood pressure detection means 52 positioned at a blood pressure detection site selected by the user. Those skilled in the art will recognize that various limbs or other locations may be used to detect the blood pressure of a patient. The detection site is typically controlled by the nature of the operative surgery or the nature of the patient's condition at the time the blood pressure is to be measured. As here illustrated, the blood pressure detection means 52 is a conventional blood pressure wrap for securing about the upper arm of a patient. The blood pressure detection means 52 is connected by appropriate tubing 54 to the chassis 36. Inflation means are connected through the chassis to the blood pressure detection means via appropriate tubing 56. The inflation means is here shown to be a conventional squeeze bulb 58 with valve 60. Indication means 62 are positioned on the chassis 36 to indicate the actual blood pressure upon operation of the blood pressure detector means. The blood pressure measuring means also has associated therewith a Korotkoff sound detection device 64 connected by appropriate tubing 66 to the chassis 36 in order to process and provide Korotkoff sounds when blood pressure is being sensed. The Korotkoff sound detection device, as here illustrated, may be simply the head of a conventional stethoscope with interconnecting tubing 66 to the chassis 36.

Figure 2:
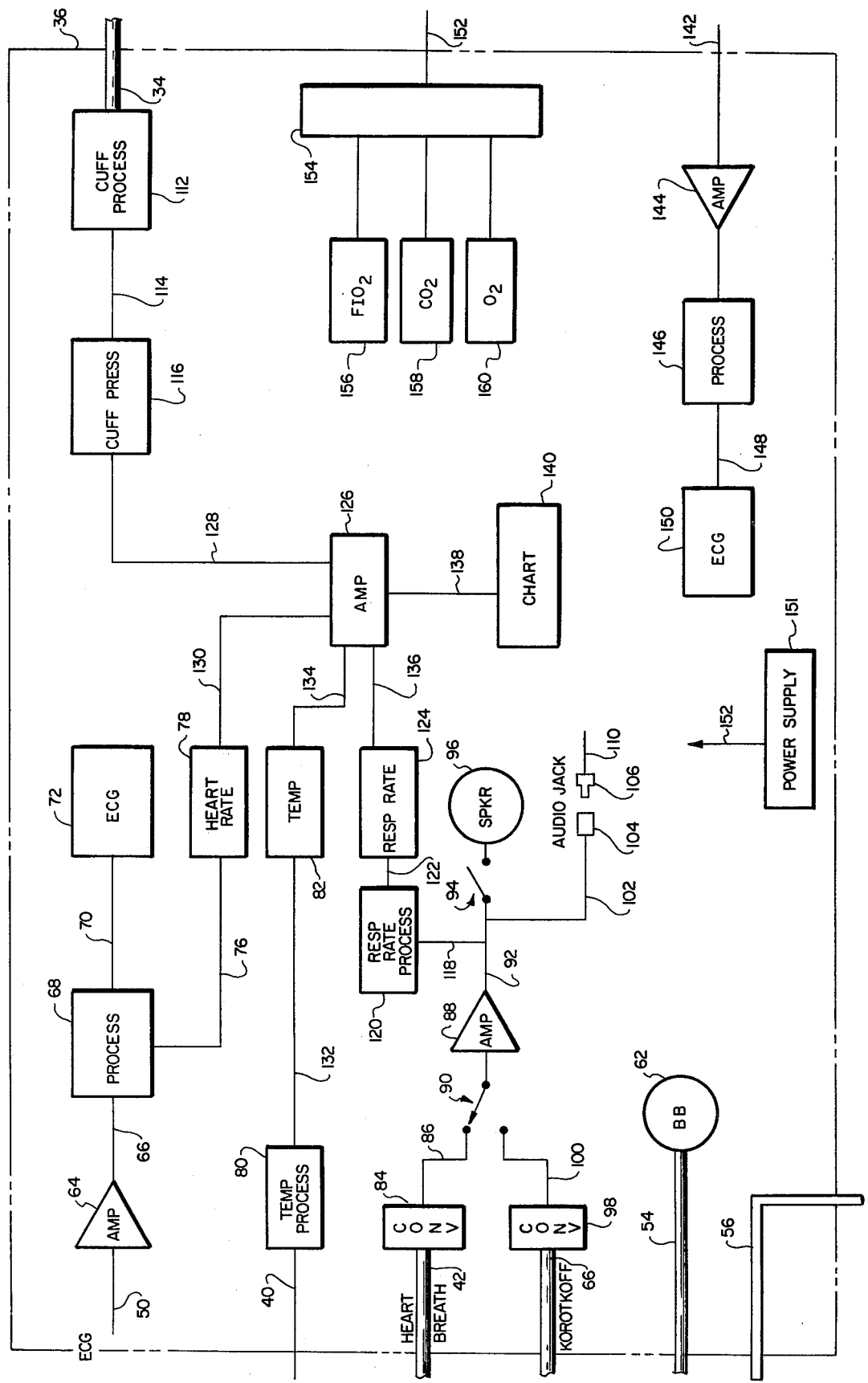
FIG. 2 is a block diagram of chassis components for use in a vital signs monitoring apparatus of the instant invention.

FIG. 2 is a simplified block diagram of the chassis 36. As can be seen, the ECG signal is received via conductor means 50 and processed through an amplifier 64. The output of the amplifier 64 is supplied via conductor 66 to a conventional ECG processing circuit 68. The output of the processing circuit 68 is supplied via conductor means 70 to an ECG scope 72 or other display device. The scope 72 is mounted on the face 74 of the chassis 36 for visual observation by the user. The output of the processing circuit 68 is also supplied via conductor 76 to a heart rate indicator 78. The heart rate indicator is also positioned on the face 74 of the chassis 36 for visual observation by the user.

The chassis 36 also receives an input from the temperature sensing means via conductor 46. The temperature sensor may be any one of a variety of different thermistors or temperature sensitive resistors supplying a temperature signal for direct readout on a temperature indicator. In some circumstances, it may be desirable to process the temperature signal in processing circuitry 80 and convert the temperature signal into a digital signal or into a more useful signal to drive an indicator 82.

As hereinbefore indicated, the heart and breath sounds are supplied to the chassis 36 via a tube 42. As here indicated, the heart and breath sounds are supplied to a converting device 84. The converting device may be a simple microphone or any other transducing device to convert the mechanical sound energy in the tube into an electrical signal for further transmission via conductor 86 to the amplifier 88 via a switch 90. The output of the amplifier 88 is supplied via conductor 90 of the output conductor 92 and another switch 94 to a conventional audio speaker 96. The Korotkoff sounds are also received via a tube 66. They are received by a converter 98 (e.g., transducer) in order to convert them from mechanical sound energy in the tube to an electrical signal transmittable via conductor 100 and the switch 90. The switch 90 is a two-position switch to allow the user to select between Korotkoff sounds and heart and breath sounds. If the heart and breath sounds and Korotkoff sounds were to be received simultaneously there would be some confusion as to the source as well as to the ability to understand and detect usable information. Parallel channels cound be used. However, it is preferred to use a single electrical channel receiving input from the heart and breath sounds and to switch therebetween with a switch as indicated at 90. The switch 94 is a single pole-throw switch to either turn on or turn off a speaker 96. In some circumstances, it may be distractive to surgeons performing an operation on a patient to have various additional audio sounds in the operating room environment. It may conflict with other necessary sounds or communications in the operating room. Thus, it is available to the user to select either an "on" or an "off" (shown) position. At the same time, an alternate lead 102 is provided to an audio jack 104 for removable connection to a jack 106. The jack 106 is further connected to an ear plug 108 (FIG. 1) by a conductor 110. Thus, in use, the ear plug may be placed in the ear of the user so that he may personally monitor the Korotkoff and heart and breath sounds without intefering with other sounds in the operating room environment or any particular environment involved.

FIG. 2 also illustrates the input line from the conventional blood pressure detection means 52 and the blood pressure gage 62. The line 56 connecting the blood pressure squeeze bulb 58 to the blood pressure sensing means 52 is also shown.

The cuff pressure sensing tube 34 is connected to a cuff processing circuit 112. The cuff processing circuit is a simple transducer to convert the pressure present in the tube 34 to an output electrical signal reflective of the pressure in the line 34 which is in turn reflective of the pressure in the cuff 20 on the end 12 of the endotracheal tube 10. The output signal of the cuff processing circuitry 112 is supplied via conductor 114 to a cuff pressure indicator 116 which is positioned for visual monitoring by the user (FIG. 1).

The actual respiration rate of the patient is also a desirable fact to be known by the user. The respiration rate may be noted audibly by the detection of the breath sounds. The visual display of the actual respiration rate and the number of breaths taken per minute or based on some other time base is desirable. The breathing sounds have a specific finite frequency spectrum which can be readily detected. From the output of the audio amplifier 88, a connection is made via conductor 118 to a respiration rate processing circuit 120. The respiration rate processing circuit 120 detects the presence of a certain frequency spectrum relating to the occurrence of a breath and supplies and measures the number of occurrences of the frequency spectrum and in turn generates an output signal reflective of the respiration rate via conductor 122 for the respiration rate indicator 124 which is positioned on the face 74 of the chassis 36.

A recording chart 140 may be included in the chassis 36. This chart may be a simple pencil-line chart of conventional design and readily available and known to those skilled in the art. The chart may have an amplifying circuit 126 which receives selective inputs. As here shown, the chart amplifier 126 receives an input from the cuff pressure processing circuit 112 via conductor 114 and conductor 128. It also receives a heart rate signal via conductors 76 and 130. It receives the temperature signal via conductors 132 and 134. The respiration rate signal is received via conductors 122 and 136. The amplifier 126 supplies its output signal via conductor 138 to the chart 140. As indicated, the chart is a pencil-line recorder of conventional design and known to those skilled in the art. It will record in a pencil-line fashion an integrated signal reflective of the existence of selected parameters over a period of time. Other parameters are additionally and similarly recorded on the chart as desired by the user.

The chassis 36 may also include other indicating parameters. In some circumstances it may be appropriate to have an external ECG (electrocardiogram) indicating device in parallel with the ECG detection system comprised of the ECG detectors 48A and 48B and the conductor 50, amplifier 64 processing the ECG signals for display on the ECG scope 72. The surface detectors may be placed on the surface of the skin in a conventional fashion, the output of which is supplied via conductor 142 to an amplifier 144 and an ECG processing circuit 146 for further transmission via conductor 148 to an external ECG display 150.

As hereinbefore noted, an external respiratory system 18 is used to supply oxygen and to monitor the $CO_2$ output from the patient. Various detection means may be placed or associated with the external respiration system 18 to detect various respiratory system parameters. Thus, detectors are connected by connector means 152 to the chassis 36. The output of those detectors are amplified or processed by appropriate means 154. The output of the processing is supplied to appropriate indicator means 156, 158 and 160, which here illustrates the $FIO_2$, the carbon dioxide and oxygen parameters related to the conventional respiration system. If desired, the output of the $FIO_2$, carbon dioxide and oxygen indicating signal processing circuitry may also be supplied by conductors to the chart 140 by conductors not shown.

FIG. 2 also illustrates the power supply 151 which supplies electrical power to the various components within the chassis 36 via representative conductor 152. All connections are not shown for simplicity sake. The power supply is any conventional battery powered circuit known to those skilled in the art to supply the necessary electrical signals to the circuits within the chassis.

It may be noted that heart sounds and breath sounds are here detected through a membrane 40. In effect, the heart sounds and breath sounds are detected by the inflatable cuff 20 and transmitted through a channel formed in the sidewall of the endotracheal tube 10 and through the external connecting tube 22 to the membrane 40. It may be also noted that the heart sounds and breath sounds may be detected by a microphone, such as a graphite pickup or a crystal pickup or any similar sound detecting device, including the simple air to electrical transducer placed proximate the interior end 12 of the endotracheal tube 10. It may also be noted that the heart sounds and breath sounds may also be detected directly from the mainline connected to the respiration system 18. That is, a simple tube may be connected, adapted or formed into the respiration connecting tube 16. This tube 170 may be connected to the chassis 36 in a similar fashion as tube 42. The preferred connection is through the cuff inflating tube 22. The respiration system noises, including the air rushes associated therewith, are considered to be too noisy and would otherwise overpower and interfere with the clarity of the sound to be received therethrough. However, it is recognized that an appropriate filter may be used to eliminate such noises and in turn produce a clear and discernible sound of use. The cost of such filters is regarded as presently prohibitive.

Referring now to FIG. 3, an interior end similar to interior end 12 of the endotracheal tube 10 is shown in axial cross-section. The endotracheal tube has an inflatable cuff 20, as shown in FIG. 1. The inflatable cuff forms a volume 180 when inflated which has a port 182 in communication with a channel 184 formed in the sidewall 186 of the tube 10. The channel 184 extends along the length of the tube to the exterior or distal end 14 for connection to the tube 22, as shown in FIG. 1. A temperature sensing means 44 may be placed on the outside surface 189 of the tube 10. The temperature sensor 44 is preferably positioned on the interior surface 190 of the cuff 20. The temperature signal transmission means is here shown to be a fine wire 192 formed into the sidewall 186 of the tube 10 to extend along the length thereof for further connection or extension as conductor 46.

A second cuff 192 is shown in FIG. 3. The second cuff has positioned on its exterior surface the mylar strips 48A and 48B. The mylar strips are connected by thin conductors 194A and 194B which extend into the sidewall 186 of the tube 10 and further extend along the length thereof to the exterior end 14 for further extension as conductors 50 to the chassis 36. Conductor 50 is shown as a single line, although it may be a multi-conductor wire, as known to those skilled in the art. The second cuff 192 has a port 196 in communication with a channel 198 which extends along the length of the tube 10 for inflation and deflation by inflation means similar to the inflation means used for conventional endotrachial tube cuff and similar to the inflation and deflation means shown in FIG. 1. The sound sensing means to hear heart sounds and breath sounds may be positioned within the second inflatable cuff 192. The sound sensing means is here shown as a graphite microphone disk 200 with a wire conductor 202 extending away therefrom. The wire conductor 202 extends along the length of the endotracheal tube 10 for direct connection through an external wire (not shown) to the switch 90, shown in FIG. 2, in lieu of the heart and breath sounds tube 42 through the conversion device 84. In other words, the heart and breath sounds may be detected and transmitted as mechanical sound energy through any one of several means. It may be detected in the endotracheal tube cuff 20 and transmitted through the channel 184 and through the membrane 40 and tube 42 to conversion device 84. Similarly, it may be transmitted through the channel 198 through a similar connector 24 and membrane 40 and a tube similar to tube 42 to the conversion device 84. It may also be picked up through a mechanical sensing device such as a transducer, graphite microphone or similar sound sensing device and transmitted via a wire conductor directly to the chassis 36. Finally, the heart sounds and breath sounds may be detected directly from the main air passage by a tube previously discussed as tube 170. It may be also noted that the mylar strips 48A and 48B may be positioned on the first tube cuff 20. In some circumstances, and particularly for an endotracheal tube to be used for small children and perhaps even for babies, an inflatable endotracheal tube cuff to effect a seal is not typically provided. A small cuff to insure contact of the ECG mylar strips with the interior surface of the trachea may thus be preferred under such circumstances.

FIG. 4 shows a cross-section normal to the basic axis 204 of the tracheal tube 10. FIG. 5 shows a cross-section normal to axis 205 for the tracheal tube illustrated in FIG. 3. FIG. 5 shows an alternate cross-section in which a conventional endotracheal tube with a cuff has the appropriate wires affixed or associated therewith along the external surface 206 by an appropriate laminating surface positioned thereover and thereabout 208.

It may be noted that the vital signs monitoring apparatus herein disclosed has a variety of different advantages which are unique and highly useful. In particular, the device is simple, small and compact. It allows the user, and in particular an anesthesiologist, to obtain vital signs data in a centralized location and places the output displays in a position where they can be monitored continuously without interfering with the normal functions of an anesthesiologist. In addition, the device is capable of adding as many vital sign-type information detecting devices as desired. Devices heretofore known are cumbersome and not necessarily reliable. Each particular vital sign is monitored by a particular different system which must be monitored separately and individually requiring time, attention and concentration which may be somewhat inconsistent with basic human engineering. The device disclosed permits the anesthesiologist to constantly monitor, evaluate and diagnose the basic vital physiological signs of the patient, including his heart rate, breath sound, blood pressure and other perhaps less often but equally important parameters such as temperature, ECG, type of ventilation, anesthetic mixture and so forth. This permits the anesthesiologist to look at the patient because the chassis is positionable proximate the patient. It permits the anesthesiologist to continuously listen to the heart sounds and breath sounds and also to monitor Korotkoff sounds when taking blood pressure on a regular basis. The device is powered by a simple battery which in turn makes the unit portable. Thus, during the operation it is not further encumbering to the operating room environment with wires and the like. Subsequent to the operation it remains connected during the patient's transport to a recovery room or intensive care room for connection to perhaps other monitoring apparatus. There is a known percentage of patients who, by virtue of their not being monitored, have suffered trauma and occasionally death during the transporting process. The portable battery operated device as herein disclosed facilitates monitoring of the patient during transport and in turn will permit prompt action to minimize the post-operative morbidity rate.

It is to be understood that the embodiments of the invention above described are merely illustrative of the application of the principals of the invention. Reference herein to details of the illustrated embodiment is not intended to limit the scope of the claims, which themselves recite those features regarded as essential to the invention.

I claim:

1. Tracheal life signs monitoring apparatus comprising:
    an endotracheal tube for positioning in the trachea of a patient, said tube having a proximal end and a distal end;
    inflatable structure mechanically coupled to said tube proximate said proximal end to detect the heartbeat sounds and breath sounds of a patient, said inflatable structure being adapted to inflate to form a seal between said trachea and said tube;
    transmission means which is a channel formed in said tube for communicating an inflating substance to and from said inflatable structure and to transmit said heart and breath sounds through said substance; and
    transmitting means removably connected to the transmission means proximate the distal end of said tube to receive said heart and breath sounds and transmit them for audible monitoring by the user.

2. The apparatus of claim 1 wherein said inflatable structure is an inflatable cuff and wherein said audio conversion means is a membrane positioned within said connector.

3. The tracheal life signs apparatus of claim 1 wherein said transmitting means includes:
    connecting means connected to the distal end of said transmission means, said connecting means having a first port and a second port;
    operation means connected to said first port for operation by the user to inject and extract said substance to inflate and deflate said inflatable structure;
    audio conversion means connected to said second port to receive the second signals from the substance and convert them to audible signals.

4. The tracheal life signs monitoring system of claim 3 further including temperature sensing means positioned proximate the proximal end of the tube to sense body temperature and supply signals reflective thereof, ECG sensing means positioned proximate the proximal end of the tube to sense and transmit ECG signals, and a chassis adapted for positioning proximate the patient, said chassis having means associated therewith to receive said ECG signals and derive and display selected ECG data, having means associated therewith to receive and display body temperature signals and having means associated therewithin the receive and transmit the heart and breath sounds for audible monitoring.

5. The tracheal life signs monitoring apparatus of claim 1 further including connector means interconnected in said transmitting means to sense the pressure of said substance and means connected to said connector means to sense and display the pressure of said substance.

6. For use with an endotracheal tube of the type having an inflatable cuff positioned proximate a proximal end of said tube and means to inflate and deflate said cuff with a fluid connected by communication means to said distal end of said tube, connector means connected to said communication means between said distal end and said inflate and deflate means, and means connected to said connector means to sense the pressure of said fluid and supply an electrical signal reflective thereof, and means to receive said electrical signal and continuously graphically display the pressure of said fluid.

7. A vital signs monitoring system comprising:
    an endotracheal tube having an inflatable cuff, a distal end and a proximal end;
    inflating means connected to said cuff by communication means for inflating and deflating said cuff with a fluid;
    connector means interconnected in said communication means;
    display means interconnected to said connector means to sense and display the pressure of said fluid;
    sound detection means positioned proximal the proximal end of said tube to detent the heart and breath sounds of a patient and to transmit signals reflective thereof;
    transmission means mechanically associated with said tube to transmit said heart and breath sounds to said distal end;
    means positioned proximate the distal end of said tube to receive said heart and breath sound signals and to transmit them for audible monitoring; and
    wherein said sound detection means is said cuff and said transmission means is said fluid.

8. The vital signs monitoring system of claim 7 further including a chassis adapted for positioning within aural and visual range of a user, said chassis having associated therewith said means to receive and transmit said heart and breath sounds and said display means.

9. The vital signs monitoring system of claim 8 further including blood pressure measuring means for selectively measuring a patient's blood pressure including:
    blood pressure detection means for positioning at a blood pressure detection site;
    a pressure bulb connected to said chassis for operation by the user;
    a blood pressure indicator positioned within said chassis to visually display blood pressure; and
    tubing interconnecting said blood pressure detection means, said indicator and said bulb for operable communication of pressures therebetween.

10. The system of claim 9 further including:
    electrocardiogram (ECG) sensing means adapted to said tube proximate said proximal end to sense ECG signals of a patient;
    first conductor means structurally associated with said endotracheal tube and conductively connected to said ECG sensing means to extend therefrom along the length of said tube and away from said distal end;

a power supply positioned with said chassis;

ECG display means associated with said chassis to receive, process and visually display ECG signals, said ECG display means being conductively connected to said first conductor means to receive ECG signals therefrom and to said power supply to receive power therefrom.

11. The system of claim 10 further including:

temperature sensing means adapted to said endotracheal tube proximate said proximal end to sense body temperature of a patient and supply signals reflective thereof;

second conductor means structurally associated with said endotracheal tube means and conductively connected to said temperature sensing means to receive temperature reflective signals therefrom, said second conductor means extending along the length of said tube and away from said distal end;

temperature display means associated with said chassis to receive, process and visually display said temperature reflective signals, said temperature display means being removably connected to said second conductor means to receive temperature reflective signals therefrom and to said power supply to receive power therefrom.

12. The vital signs monitoring system of claim 11 wherein said communication means is connected to means associated with said chassis to receive and transmit the heart and breath sound signals for audible monitoring.

13. The system of claim 12 wherein said blood pressure measuring means includes Korotkoff sound detection means positioned proximate said blood pressure detection means, means connected to said Korotkoff sound detection means and removably connected to said chassis to transmit said Korotkoff sounds thereto, and means within said chassis to receive said Korotkoff sounds and to transmit them for audible monitoring by the user.

14. The system of claim 13 wherein said power supply is a battery positioned within said chassis.

15. The system of claim 13 wherein said chassis has an audio speaker for broadcasting said Korotkoff sounds and the heart and breath sounds, and wherein said chassis has means operable by the user to switch the sounds broadcast on said audio speaker between Korotkoff sounds and the heart and breath sounds.

16. The system of claim 13 wherein said chassis further includes means to extract heart rate signals from said ECG signal and means to visually display heart rate signals.

17. The system of claim 13 wherein said chassis has means to detect respiration rate signs from said ECG signal and means to visually display respiration rate signals.

18. The system of claim 13 wherein said chassis has graphic recorder means and means to receive selected signals and display same graphically on said recorder.

19. The system of claim 13 wherein said chassis means transmits selectively said Korotkoff sounds and the heart and breath sounds to a portable earphone removably connectable to said chassis and positionable proximate the ear of a user.

20. The system of claim 13 wherein said exterior end of said endotracheal tube is connected to respiration apparatus and wherein detection means is associated with said respiration apparatus to detect selected respiration system parameters, means are connected to said detection means and said chassis to transmit the detected parameters to said chassis and display means on said chassis to visually display said selected parameters.

* * * * *